United States Patent [19]
Johnson, Jr. et al.

[11] Patent Number: 5,387,185
[45] Date of Patent: Feb. 7, 1995

[54] KNEE IMMOBILIZER SPLINT

[75] Inventors: Glenn W. Johnson, Jr., Summit; Henry J. McVicker, Chatham, both of N.J.

[73] Assignee: Aircast, Incorporated, Summit, N.J.

[21] Appl. No.: 148,937

[22] Filed: Nov. 8, 1993

[51] Int. Cl.6 .............................................. A61F 5/00
[52] U.S. Cl. ...................................... 602/26; 602/23; 602/5; 128/882
[58] Field of Search .................. 602/5, 16, 26, 20, 23; 128/870, 882

[56] References Cited

U.S. PATENT DOCUMENTS

| 3,526,222 | 9/1970 | Dreibelbis | 128/870 |
| 3,831,467 | 8/1974 | Moore | 602/26 |
| 3,933,154 | 1/1976 | Cabansag | 128/870 |
| 4,090,508 | 5/1978 | Gaylord, Jr. | 602/26 |
| 4,111,194 | 9/1978 | Cox et al. | |
| 4,848,326 | 7/1989 | Lonardo | 602/26 |
| 5,230,335 | 7/1993 | Johnson et al. | |
| 5,267,949 | 12/1993 | DeLaTorre et al. | 128/882 X |

OTHER PUBLICATIONS

Irrgang, J. J., "Postoperative Rehabilitation Following Anterior Cruciate Ligament Reconstruction," *Clinics in Sports Medicine*, vol. 12, No. 4, Oct. 1993, pp. 807–813.
Knee Immobilizers, Zimmer, 1989, product brochure.
Tecnol, Inc., Orthopedic Soft Goods, pp. 22–23, product brochure, undated.
Watco Orthopedics, The Wonderbrace Series, 1992, product brochure.
Watco Products, Inc., "Design and Manufacture of Orthopaedic Specialities," pp. 1–10, product brochure, undated.

Primary Examiner—Richard J. Apley
Assistant Examiner—Linda C. M. Dvorak

[57] ABSTRACT

A hingeless splint that provides immobilization of the knee in varying degrees of extension or maximal extension. The device is mostly open around the knee for comfort and permits convenient application of supplemental cold and compression dressings to be used therewith.

12 Claims, 3 Drawing Sheets 5,387,185

KNEE IMMOBILIZER SPLINT

FIELD OF THE INVENTION

The present invention relates in general to a knee immobilizer splint and in particular to an immobilizer splint that can be used for optimal extension and maximal extension of the knee.

BACKGROUND OF THE INVENTION

It is well known in orthopedics to immobilize a knee in extension for protection after injury or surgery, and numerous commercial devices are available for this purpose. One family of such devices use a series of multiple stays with close fitting panels and straps to keep the leg in the normal neutral position, offered by the Tecnol Company. Other similar devices offer an immobilizer molded as a plastic shell that conforms generally to the posterior of the limb, with four extension arms retaining straps for attachment of the device to the leg (such as offered by Watco Products Inc., depicted in U.S. Pat. No. 4,111,194, issued Sep. 5, 1978.). Other types of more expensive or complicated hinged braces also are available.

However, to applicant's knowledge, all such prior known devices are designed to keep the knee in a neutral or even a slightly flexed position. Further, all such devices are designed for close contact with the knee and the leg, leaving little room for accommodation of any supplemental cold and compression type dressings which have proven in recent years to advance healing.

In recent years it has become known that recovery after some types of surgery, such as anterior cruciate ligament reconstruction (ACL) is enhanced if the knee is kept in extension or maximal extension equal to that attainable in the opposite healthy leg. Such full extension it is believed precludes the formation of scar tissue within the joint during the initial healing period and helps insure a full range of motion after recovery.

Loss of motion (LOM) has recently been recognized as the most common complication following ACL reconstruction. A 24% incidence of a knee flexion contracture greater than 5 degrees following ACL reconstruction has been reported. This finding correlated positively with quadriceps weakness and patellofemoral pain. LOM is defined as a knee flexion contracture greater than or equal to 10 degrees or knee flexion less than 125 degrees or both. All patients with LOM experienced loss of extension and two thirds also had an associated loss of flexion. Patients who developed LOM used a postoperative brace that limited full extension more often than patients who had normal motion following surgery. This loss of full extension following ACL reconstruction may have adverse functional implications that may lead to an abnormal gait, quadriceps weakness, or patellofemoral pain. This recently has been reported in the "The Anterior Cruciate Ligament;" by Freddie H. Fu, M.D., *Clinics in Sports Medicine*, Vol. 12, No. 4, October 1993.

Postoperative management following ACL reconstruction to reduce the risk of LOM emphasizes inter alia early restoration of full extension symmetric to the noninvolved knee, early range of motion and quadriceps exercises, and restoration of normal gait. Cold and compression, (such as that provided by the Cryocuff TM (produced by applicant's assignee Aircast Inc., Summit, N.J.)), also are used to reduce postoperative inflammation.

The appropriate amount of knee extension is highly individual and may vary during the early period of post operative recovery. None of the known non-hinged immobilizers is capable of providing this highly desirable, individualized maximal extension of the leg in a convenient and cost effective manner.

OBJECTS OF THE INVENTION

It is a primary object of the invention to provide immobilization of the knee in varying degrees of extension or maximal extension in a hingeless splint. It is a further object of the invention to provide such a knee immobilizing splint that is generally open around the knee for comfort and to permit convenient application of supplemental cold and compression dressings such as those disclosed in commonly assigned U.S. patent application Ser. No. 644,835, filed Jan. 23, 1991 and entitled "Thermal Compress System."

SUMMARY OF THE INVENTION

The present invention not only provides immobilization of the knee in varying degrees of extension or maximal extension in a hingeless splint, but also provides a splint for immobilizing the knee that is mostly open around the knee for comfort and that permits convenient application of supplemental cold and compression dressings to the knee with the immobilizer applied.

In a preferred embodiment, the immobilizer splint is formed of a spine that is relatively rigid and is formed preferably of stiff aluminum. The length of the spine will depend on the length of the leg and may come in various predetermined lengths for use with various sized individuals.

At about the knee, the spine is bent forwardly about 5 degrees from the vertical so as to increase the clearance between the back of the knee and the splint when the splint is placed with the included angle of 175° facing the rear or posterior of the knee. The opposite ends of the spine also may be bent slightly in the opposite direction to avoid any sharp contact with the flesh of the person using the device.

A frame, preferably formed of flexible plastic, such as polyethylene, is shaped to cover the spine and to tether a plurality of straps for attachment of the splint to the leg. The frame can be attached to the spine with rivets or with adhesive. A liner is attached to frame opposite the spine; with adhesive, and is formed from a cushioning material such as foam material, intended to contact the user's leg.

The straps for attaching the splint to the leg may consist of at least four straps attached in spaced relationship with each other on one side of the frame with D-ring construction, and hook and loop type material such as that sold commercially under the trademark VELCRO on the strap so the straps can slip through the D-rings, overlap themselves, and be adjusted in tightness. It is preferable to have every other strap assembled in the opposite direction so tightening forces are neutral.

Thus the present invention relates to a hingeless knee immobilizer splint for optimal extension of the knee of the leg, comprising a single elongated rigid spine for longitudinal alignment with the posterior of the leg and extending above and below the knee such that a space exists between the rigid spine and substantially the back of the knee, and has at least one pair of fastening straps coupled to the rigid spine both above and below the knee for holding the rigid spine in longitudinal alignment at the back of the leg such that, by tensioning at least one strap, pressure is supplied to the anterior aspect of the leg above and below the knee into the knee extension desired. In its preferred embodiment the splint will have a predetermined inwardly directed included bend intended to provide maximal extension of the knee.

BRIEF DESCRIPTION OF THE DRAWINGS

These and other objects of the present invention will be more fully disclosed when taken in conjunction with the following detailed description of the drawings, in which like numerals represent like elements and in which.

DETAILED DESCRIPTION OF THE DRAWINGS

Figure 1:
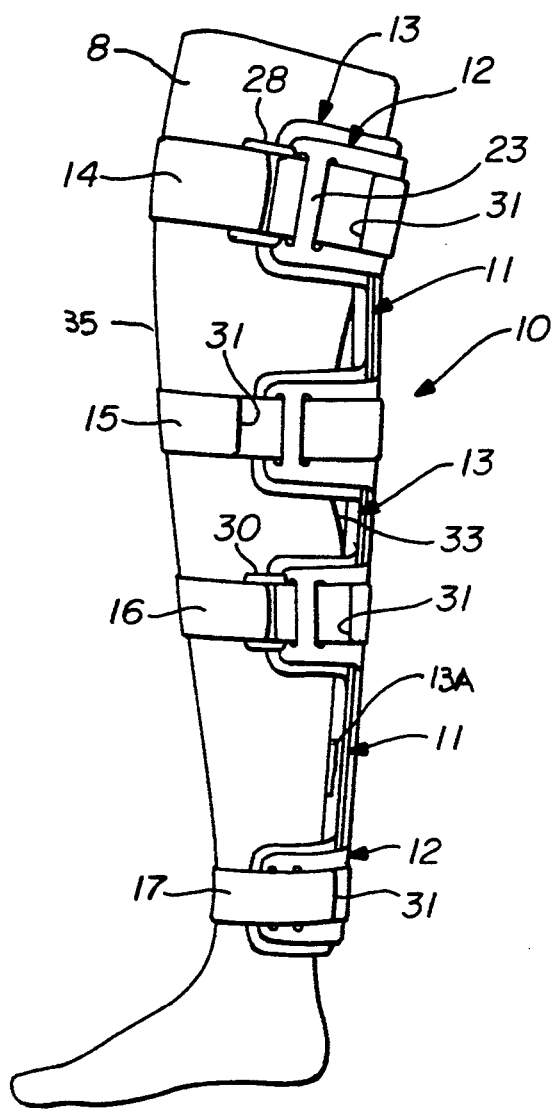
FIG. 1 is a side view of the novel knee splint immobilizer in place on a leg.

FIG. 1 is a side view of the novel knee immobilizer splint 10 in place on a leg 8. The splint 10 includes a rigid spine 11 that may be formed of stiff plastic or metal. In the illustrated embodiment the spine 11 is preferably of stiff aluminum that is about 0.375 inches in thickness, 1.5 inches in width and about 26.5 inches long for a medium size leg. A smaller size splint could be used for a small leg, where the spine 11 is about 23 inches long, or about 29.4 inches long for a longer leg (See FIG. 5). As will be seen better in relation to FIG. 4, at about 45% of the distance from one end, the spine 11 is bent upwardly about 5°, with the included angle 32 of 175° intended in use to face the posterior of the knee so as to increase the clearance between the back of the knee and the splint and also to provide maximal extension to the knee. Thus, it will be noted in FIG. 1 that a gap 31 exists between the back or posterior 33 of the knee 35 and the spine 11.

Figure 3:
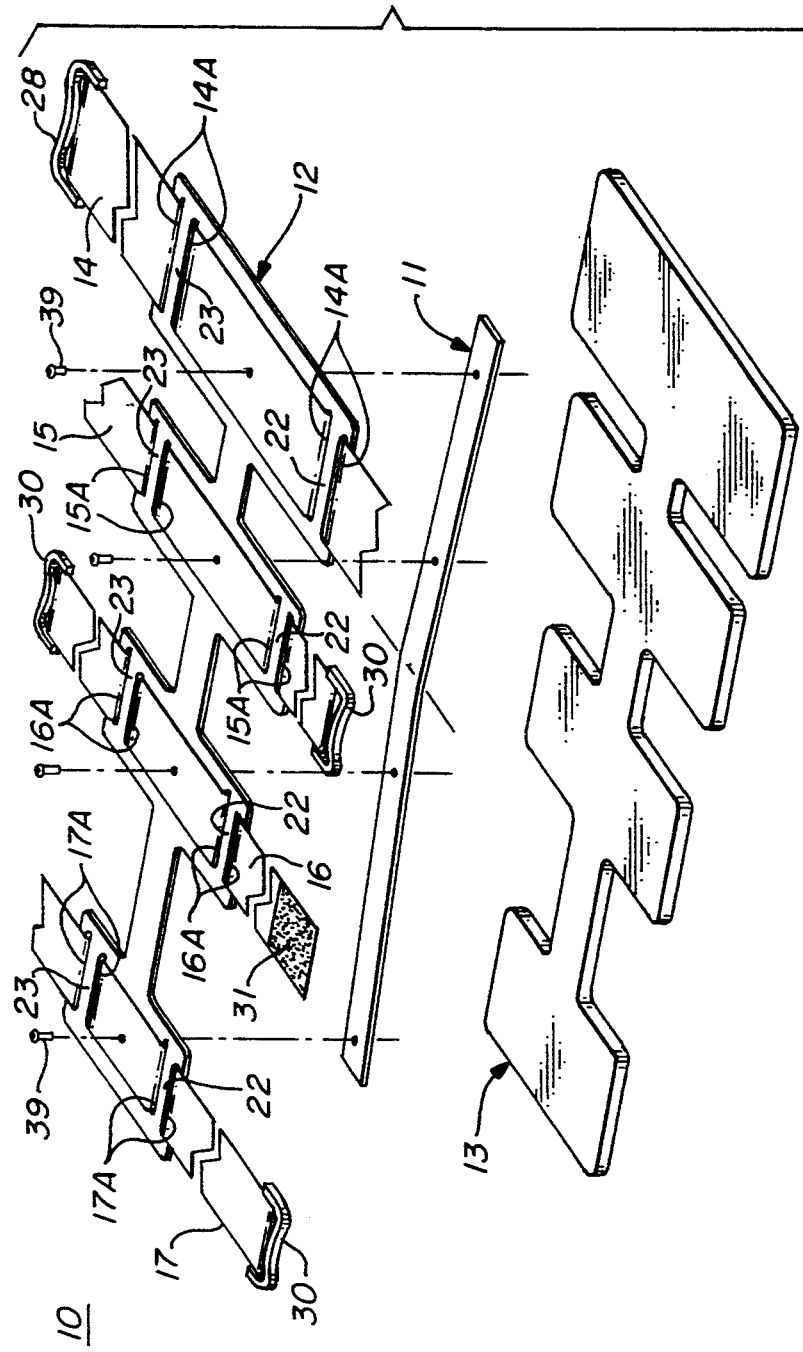
FIG. 3 is an exploded perspective assembly drawing of the device illustrating the spine, the frame, the liner and the straps thereof.
Figure 4:
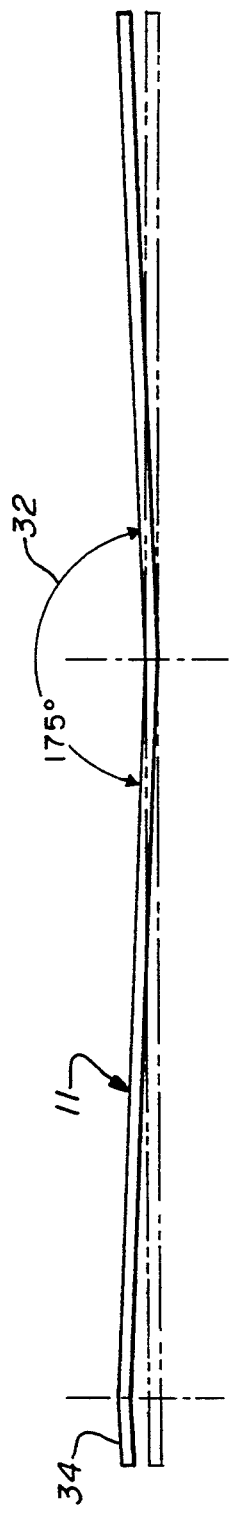
FIG. 4 is a side view of the spine of the splint, illustrating the bend at roughly mid length so as to provide maximal extension and to increase the clearance between the back of the knee and the splint.
Figure 5:
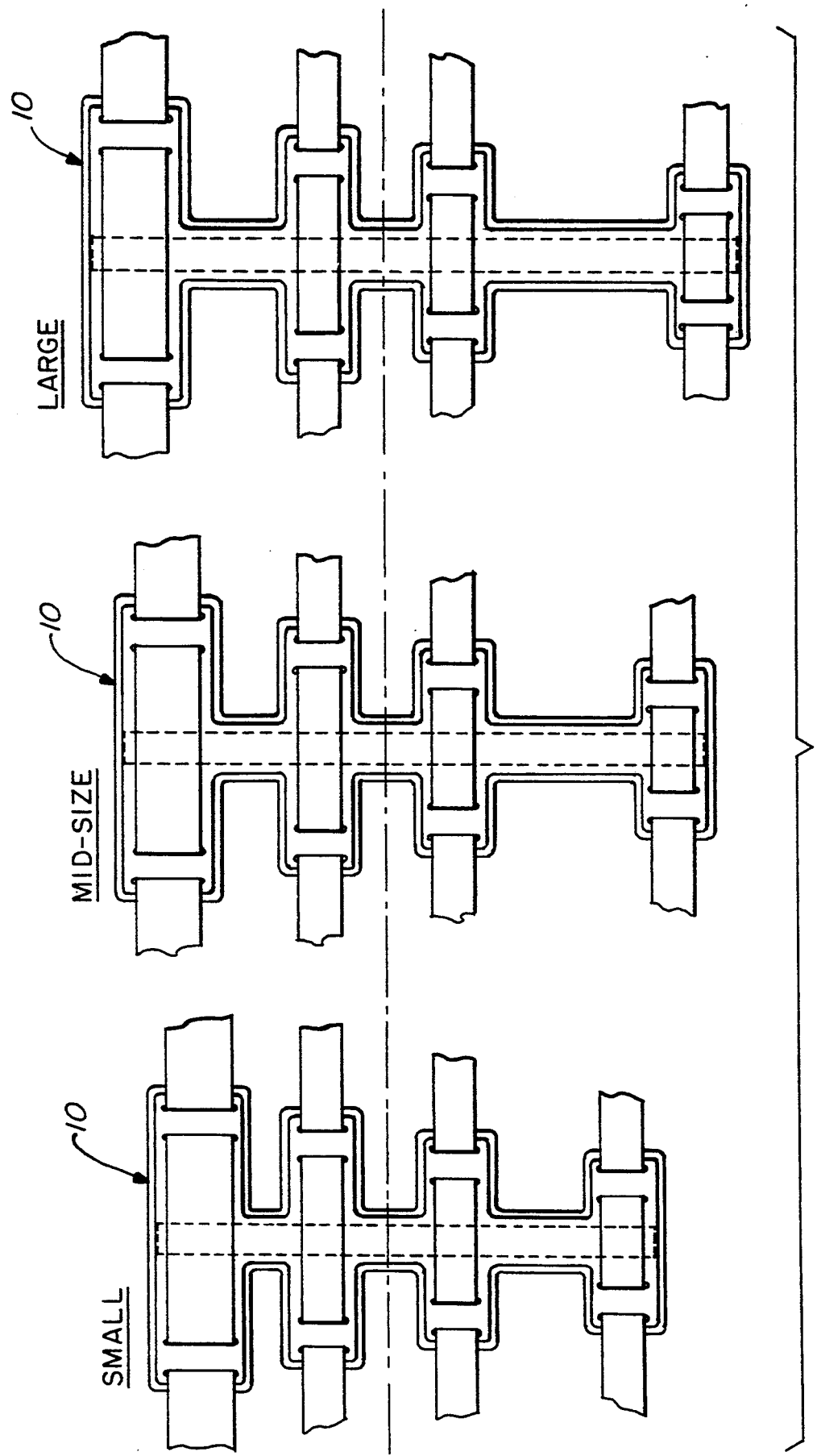
FIG. 5 is a table providing general anthropometric data for use in selecting different size splints based on various leg lengths.

A frame 12, shown more clearly in the exploded view in FIG. 3, preferably is formed of flexible plastic such as 0.060 inches thick polyethylene that is shaped as shown in FIG. 3 to cover the spine 11, and also to tether the straps 14, 15, 16 and 17, which are inserted through appropriately matching slots. The frame 12 can be attached to spine 11 with rivets 39, as illustrated in FIG. 3 or with appropriate adhesive. A liner 13 shaped as shown in FIG. 4 and made from a cushioning material such as 0.375 inch thick of a foam material such as Velfoam, manufactured by the Velcro Company is applied below the spine 11.

To minimize movement of the splint when worn, the liner 13 may be provided with a high friction material 13A such as Volextra, provided by Voltec Inc. of Lawrence, Mass., at suitable locations on the liner 13. The liner 13 may be attached to the frame 12 with adhesive, and sandwiches the spine 11 there between. The high friction material 13A also may be adhesively applied, and is preferably about 1/16" thick.

The straps 14, 15, 16 and 17 are of conventional hook and loop construction with D-rings 28 (or 30) at one end and a loop material at the other end, such that when the strap 16 is inserted into a D-ring 28, it may be wrapped back on itself so that the hook and loop material 31 engage in known fashion. It is preferable, as shown, to have every other strap 14 and 16, and 15 and 17, assembled with the D-ring in the opposite direction so that the tightening forces are neutral. Preferably, the straps also will include a portion of the high friction material to minimize movement along the leg.

In normal use, as illustrated in FIG. 1, the splint 10 is attached to a leg 8 with the liner 13 in cushioning contact with the upper leg or thigh, under the area of strap 14, and in contact with the lower leg or calf under strap 16. Because of the 5° inward bend in the spine 11, there is automatically provided some clearance between the posterior 33 of the knee 35, in the area between the straps 15 and 16. Therefore, with tensioning of straps 15 and 16, pressure is applied to the anterior aspect of the limb 8 above and below the knee joint 35 and the knee 35 is therefore pressed into extension as desired, to a maximal extension. As can be seen from FIG. 1, even without the 5° bend in the spine 11, there would be some clearance behind the knee; however, the bend assures enough clearance to accommodate a wide range in size of patients, and provides other advantages as hereinafter described.

FIG. 3 is an exploded view of the elements of the splint 10. It comprises the stiff spine 11. It also includes the frame 12, having the straps 14, 15, 16 and 17 for tightening about the leg as illustrated in FIG. 1. Strap 14 is located in the area of the thigh and is therefore the widest strap with the greatest transverse length on the frame 12. The spaced transverse portions for straps 15, 16 and 17 are somewhat narrower because they are located in areas where less pressure is required, but they still are generally wider than prior devices, to assure contact and to minimize splint movement. Thus, the strap 14 may be three inches in width and have a 30 inch length, while straps 15, 16 and 17 each may have a 2 inch width with strap 15 having a length of 20.5 inches, strap 16 having a length of 25.5 inches and strap 17 having a length of 18 inches. Of course these are examples only and could be varied as needed for a particular sized leg. The straps 14, 15, 16 and 17 thread under loops 22 and 23 defined by slots 14A, 15A, 16A and 17A provided in the polyethylene frame 12. Rivets 39 may be used to attach each of the transverse areas of the frame 12 to the spine 11. Appropriate sized D-rings 28 and 30 may be used with the straps 14, 15, 16 and 17 such that each strap can be threaded through the "D" ring and pulled backwards over itself so that the hook and loop material will attach the strap to itself and hold it in the desired fixed position. The liner 13 is shaped as shown in FIG. 2 to cover the spine 11 and the tethered straps 14, 15, 16 and 17.

The liner 13 is formed from a cushioning material such as 0.375 inches thick of foam material.

Figure 2:
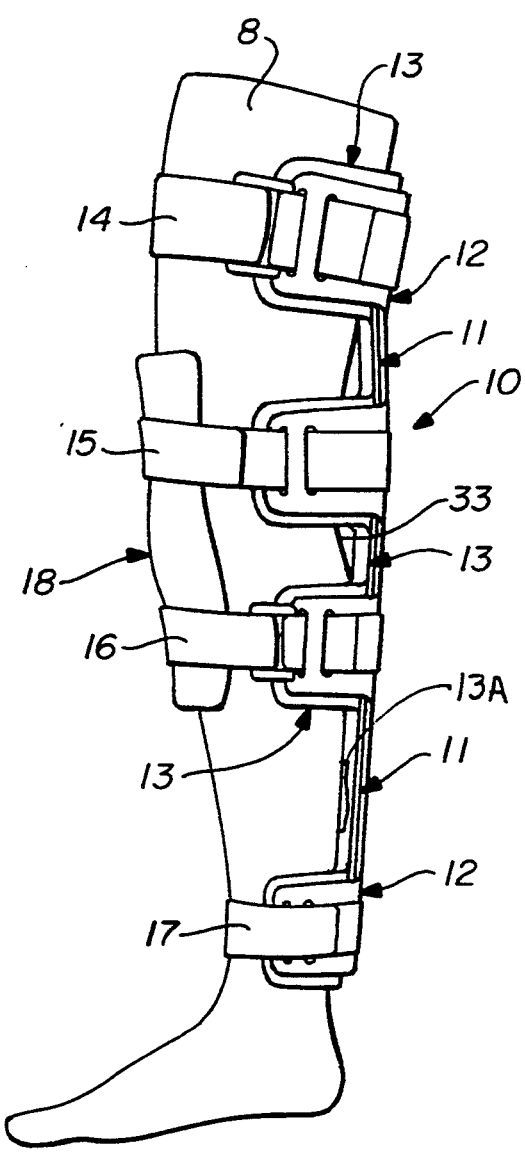
FIG. 2 is a similar side view of the novel splint on a leg, with the device holding a dressing for applying cold and compression.

FIG. 2 is a side view of the splint 10 attached to the leg 8 with a Cryocuff ™ dressing 18 of the type disclosed in said application Ser. No. 644,835, normally retained by the pair of straps 15 and 16 to maintain the dressing 18 in place without any compression at the back of the knee. This of course permits significant compression around the suprapatella area where it is needed without any pressure at the back of the knee 33 where the pressure is unneeded and in fact, may be harmful.

FIG. 4 is a side view of the novel spine 11 illustrating the 5° bend slightly off center and providing an included angle 32 of 175°. If desired, one or both ends of the spine 11 may be bent backwards in the opposite direction, as illustrated at 34, to avoid sharp contact with the thigh and ankle.

Thus there has been disclosed a novel splint that provides for immobilization of the knee in varying degrees of extension and in maximal extension. The splint does not have any hinges. Further, the knee immobilization is mostly open around the knee for comfort, and also permits convenient application of supplemental cold and compression dressings thereto.

In the preferred environment the spine is stiff aluminum about 0.375 inches in thickness, 1.5 inch in width and about 26.5 inches long for a medium sized leg. At about 45% from the thigh end, the spine is bent about 5° so as to increase the clearance between the back of the knee and the splint. The two ends of the spine may also be bent slightly in the opposite direction to avoid sharp contact with the thigh and ankle.

While the invention has been shown and described with respect to a particular embodiment thereof, this is for the purpose of illustration rather than limitation. Other variations and modifications of the specific embodiment herein shown and described will be apparent to those skilled in the art all within the intended spirit and scope of the invention. Accordingly, the patent is not to be limited to the scope and effect to the specific embodiment shown and described herein nor in any other way that is inconsistent with the extent to which the progress and the art has been advanced by the invention.

We claim:

1. A hingeless immobilization splint for optimal extension of the knee of a leg comprising:
    a single elongated hingeless rigid spine for longitudinal alignment with the posterior of an associated leg and having portions adapted to extend above and below the knee and having an included angle formed at about midlength thereof such that said angle provides a space between the rigid spine and the back of the associated knee; and
    fastening devices operatively coupled to said spine, both above and below the area of the spine near the associated knee, for holding said spine in longitudinal alignment at the posterior of the associated leg such that by tensioning said fastening devices, pressure is applied to the anterior aspect of the leg both above and below the knee thereby to press the knee into the desired extension, while leaving space between the rear of the knee and said spine.

2. The immobilizer splint set forth in claim 1, wherein said fastening devices are adjustable so as to enable varying degrees of extension, and maximal extension, to be applied to the knee when said fastening devices above and below the knee are tensioned.

3. The splint set forth in claim 1, further comprising:
    a flexible frame fixedly attached to said spine; and
    said fastening devices comprise a plurality of straps movably attached to said frame.

4. The splint set forth in claim 3, further including a soft pliable liner affixed to said frame and opposite said spine from said frame, thereby enveloping said spine between said frame and said liner.

5. The splint set forth in claim 2, wherein at least one end of said spine is formed at an angle opposite said first angle in said spine, to avoid sharp contact of said spine with the skin of the associated leg.

6. The splint set forth in claim 1, wherein said fastening devices further comprise:
    a first flexible strap operably attached to said spine in substantially the thigh area;
    a second flexible strap spaced from said first flexible strap and operably attached to said spine in the area corresponding to the suprapatella;
    a third flexible strap spaced from said second flexible strap and operably attached to said spine corresponding to the anterior leg area immediately below the associated knee; and
    a fourth flexible strap spaced from said third flexible strap and attached to said spine corresponding to the area of the associated ankle, such that the first and third straps may be wrapped around the leg to attach the leg brace to the leg, and said second and third straps may be wrapped around the leg to apply pressure to the anterior aspect of the knee when tensioned and permit significant compression substantially in the suprapatella area and no pressure at the posterior of the knee.

7. The splint set forth in claim 6, wherein a flexible frame is affixed to said spine and said straps are operably connected to said spine by placement through said frame, said frame including
    an elongated area for attachment to and covering the rigid spine; and
    a plurality of transverse segments integrally formed with the elongated area and respectively operatively associated with each of said four spaced straps; a first transverse segment having the greatest width and transverse length to partially encircle the corresponding thigh area and the fourth transverse segment having the smallest transverse length to partially encircle the corresponding ankle portion of an associated leg.

8. The splint as set forth in claim 1, wherein said rigid spine is formed of relatively rigid aluminum.

9. The splint set forth in claim 3, wherein said flexible frame is formed of a flexible plastic.

10. The splint set forth in claim 9, wherein said plastic is polyethylene and said frame is about 0.06 inches thick.

11. The splint set forth in claim 4, wherein said soft pliable liner comprises a 0.375 inch thick foam material attached to said flexible frame with adhesive, and wherein said liner includes a portion of a relatively high friction material positioned to contact the associated leg.

12. The splint set forth in claim 2, wherein said included angle provided in said spine is about 175° inwardly toward the posterior of the knee.

* * * * *